US012726048B2

(12) United States Patent
Kurita et al.

(10) Patent No.: US 12,726,048 B2
(45) Date of Patent: Sep. 1, 2026

(54) WIRELESS POWER SUPPLY SYSTEM

(71) Applicants: ADTEX Inc., Takasaki (JP); Kake Educational Institution, Okayama (JP); Nobuyuki Kurita, Maebashi (JP)

(72) Inventors: Nobuyuki Kurita, Maebashi (JP); Hiroo Sato, Takasaki (JP); Hiroki Ishida, Okayama (JP); Shinji Koshino, Takasaki (JP); Toru Takeda, Takasaki (JP)

(73) Assignees: ADTEX Inc., Takasaki (JP); Kake Educational Institution, Okayama (JP); Nobuyuki Kurita, maebashi (JP)

( * ) Notice: Subject to any disclaimer, the term of this patent is extended or adjusted under 35 U.S.C. 154(b) by 57 days.

(21) Appl. No.: 19/057,977

(22) Filed: Feb. 20, 2025

(65) Prior Publication Data

US 2025/0192616 A1 Jun. 12, 2025

Related U.S. Application Data

(63) Continuation of application No. PCT/JP2023/040125, filed on Nov. 7, 2023.

(30) Foreign Application Priority Data

Nov. 8, 2022 (JP) ................................ 2022-179169

(51) Int. Cl.
*H02J 50/12* (2016.01)
*A61M 60/178* (2021.01)
(Continued)

(52) U.S. Cl.
CPC .......... *H02J 50/12* (2016.02); *A61M 60/178* (2021.01); *A61M 60/232* (2021.01);
(Continued)

(58) Field of Classification Search
CPC .......... H02J 50/12; H02J 2105/46; H02J 7/00; A61M 60/178; A61M 60/232;
(Continued)

(56) References Cited

U.S. PATENT DOCUMENTS

2018/0241252 A1 8/2018 Fan et al.
2022/0385107 A1 12/2022 Assawaworrarit et al.
(Continued)

FOREIGN PATENT DOCUMENTS

JP H10-14139 A 1/1998
JP 2006-217731 A 8/2006
(Continued)

OTHER PUBLICATIONS

Z. Ye, M. Yang and P.-Y. Chen, "Multi-Band Parity-Time-Symmetric Wireless Power Transfer Systems for ISM-Band Bio-Implantable Applications," in IEEE Journal of Electromagnetics, RF and Microwaves in Medicine and Biology, vol. 6, No. 2, pp. 196-203, Jun. 2022 (Year: 2022).*
(Continued)

*Primary Examiner* — Daniel Cavallari
(74) *Attorney, Agent, or Firm* — Yokoi & Co., U.S.A.; Toshiyuki Yokoi

(57) ABSTRACT

A wireless power supply system using Parity-Time symmetry for supplying an electric power from an external device 19 installed outside a human body to an internal device 29 installed inside the human body for driving an artificial device, wherein a power transmission side resonance circuit 12 is formed by connecting a power transmission side coil 11 and a power transmission side resonance capacitor in series with each other, a power reception side resonance circuit 22 is formed by connecting a power reception side coil 21 with at least one of power reception side resonance capacitors, and resonance frequencies are matched with each
(Continued)

other between the power transmission side resonance circuit and the power reception side resonance circuit.

4 Claims, 11 Drawing Sheets

(51) Int. Cl.

| | |
|---|---|
| ***A61M 60/232*** | (2021.01) |
| ***A61M 60/411*** | (2021.01) |
| ***A61M 60/873*** | (2021.01) |
| *H01F 27/24* | (2006.01) |
| *H01F 27/28* | (2006.01) |

(52) U.S. Cl.
CPC ........ *A61M 60/411* (2021.01); *A61M 60/873* (2021.01); *H01F 27/24* (2013.01); *H01F 27/28* (2013.01)

(58) Field of Classification Search
CPC ............. A61M 60/411; A61M 60/873; A61M 60/148; A61M 60/196; A61M 60/216; H01F 27/24; H01F 27/28
See application file for complete search history.

(56) References Cited

U.S. PATENT DOCUMENTS

| | | | | |
|---|---|---|---|---|
| 2023/0314181 | A1* | 10/2023 | Tseng | G01D 5/22 324/207.15 |
| 2024/0120775 | A1 | 4/2024 | Ishida | |

FOREIGN PATENT DOCUMENTS

| | | | |
|---|---|---|---|
| JP | 2020-14497 | A | 1/2020 |
| JP | 2022-121324 | A | 8/2022 |
| WO | 2018/150678 | A | 8/2018 |
| WO | 2021/081426 | A | 4/2021 |

OTHER PUBLICATIONS

International Search Report for PCT/JP2023/040125 dated Jan. 30, 2024.

PCT written opinion dated Jan. 30, 2024.

SID Assawaworrarit, Xiaofang Yu & Shanhui Fan, “Robust wireless power transfer using a nonlinear parity-time-symmetric circuit”, Nature, Jun. 15, 2017, vol. 546, p. 387-390.

* cited by examiner supplying electric power

Figure 5A:
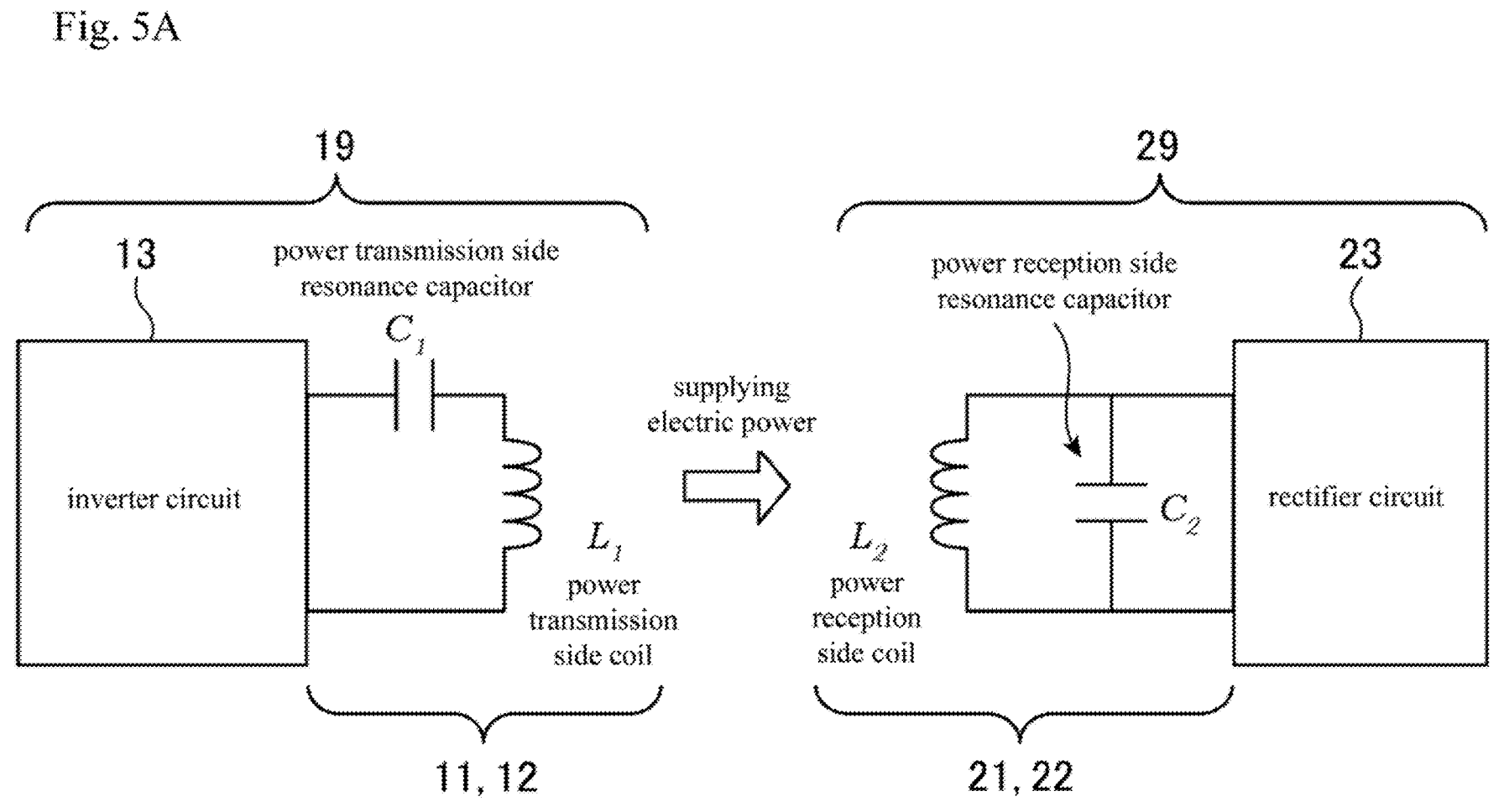

Fig. 5A 13
inverter circuit
19
power transmission side resonance capacitor
$C_1$
$L_1$
power transmission side coil
11, 12
supplying electric power
29
power reception side resonance capacitor
$C_2$
$L_2$
power reception side coil
21, 22
23
rectifier circuit 19
29
13
power transmission side resonance capacitor
$C_1$
inverter circuit
$L_1$
power transmission side coil
11, 12
supplying electric power
power reception side resonance capacitor
23
$C_{21}$
$C_{22}$
rectifier circuit
$L_2$
power reception side coil
21, 22

13
inverter circuit
19
power transmission side resonance capacitor
$C_1$
$L_1$
power transmission side coil
11, 12
supplying electric power
29
power reception side resonance capacitor
$C_2$
$L_2$
power reception side coil
21, 22
23
rectifier circuit

WIRELESS POWER SUPPLY SYSTEM

CROSS-REFERENCE TO RELATED APPLICATIONS

This application claims the benefit of priority and is a Continuation application of the prior International Patent Application No. PCT/JP2023/040125, with an international filing date of Nov. 7, 2023, which designated the United States, and is related to the Japanese Patent Application No. 2022-179169, filed Nov. 8, 2022, the entire disclosures of all applications are expressly incorporated by reference in their entirety herein.

TECHNICAL FIELD

The present invention relates to a wireless power supply system for supplying an electric power to an artificial device (implantable medical device) such as an artificial heart installed inside a human body.

BACKGROUND OF THE INVENTION

Currently, a ventricular assist device (VAD) is put into practical use for assisting blood circulation by installing a pump (electric pump) driven by a motor under a heart of a patient. In the above described case, as a power source (electric power) for driving the electric pump, it is general to make a hole in an abdomen (human body), pull an electric wire out of the human body and connect the electric wire to the power source and a controller (controller for controlling the electric pump) located outside the human body for driving the ventricular assist device (e.g., shown in Patent Document 1).

However, since the hole through which an electric wire or the like penetrates is formed on the abdomen (human body), various problems exist. For example, the patient cannot take baths or a risk of infection increases. Thus, there is a demand for applying a wireless power supply technology to an artificial device installed inside the human body to make the electricity flow (supply the electric power) in a non-contact manner.

If the patient is an adult, it is possible to personally care the hole through which the electric wire or the like used for the artificial device installed inside the human body penetrates or possible to act while caring the hole. However, if the patient is a child, special attention needs to be paid for handling the hole and a risk of infection or the like is higher. Therefore, it is more strongly desired to apply the wireless power supply technology to the artificial device such as the ventricular assist device to make the electricity flow (supply the electric power) in a non-contact manner without forming the hole on the abdomen (human body).

On the other hand, as for the wireless power supply technology in a non-contact manner, several technologies such as an electromagnetic induction system and a magnetic field resonance system conventionally exist. In the conventional technologies, the wireless power supply technology of the electromagnetic induction system is used, for example, for charging a mobile phone where coils are vertically arranged. Namely, this is exactly an electrical transformer. The electricity flows when a power transmission side coil and a power reception side coil are in close contact with each other.

However, in the wireless power supply technology of the electromagnetic induction system, it is impossible to keep the distance between the power transmission side coil and the power reception side coil large. In addition, the charging and the power transmission become impossible if the power transmission side coil and the power reception side coil are even slightly displaced or separated. Therefore, it is difficult to apply the wireless power supply technology of the electromagnetic induction system to the artificial device such as the artificial heart installed inside the human body.

Furthermore, the wireless power supply technology of the magnetic field resonance system is developed at a university in U.S. around 2006 to 2007. The distance between the power transmission side coil and the power reception side coil can be larger compared to the electromagnetic induction system. Thus, the wireless power supply technology of the magnetic field resonance system is at a level close to practical application. However, the electricity cannot be transmitted unless the distance between the power transmission side coil and the power reception side coil is kept constant. The electricity cannot be transmitted if the distance decreases, the distance increases or the angles are different. Due to the above described sensitivity, it is also difficult to apply the wireless power supply technology of the magnetic field resonance system to the artificial device such as the artificial heart installed inside the human body.

For solving the above described problem, Patent Document 2 discloses, for example, the wireless power supply technology of the magnetic field resonance system including a controller having the function of adjusting the positional relation and the angle between the power transmission side coil and the power reception side coil for stably supplying the electric power to the artificial heart or the like.

PRIOR ART DOCUMENTS

Patent Documents

Patent Document 1: Japanese Patent Application Publication No. 2020-14497

Patent Document 2: International Patent Application Publication No. 2018/150678

Patent Document 3: Japanese Patent Application Publication No. 2022-121324

Non-Patent Documents

Non-patent Document 1: Sid Assawaworrarit, Xiaofang Yu & Shanhui Fan, "Robust wireless power transfer using a nonlinear parity-time-symmetric circuit", Nature, 15 Jun. 2017, volume 546, p. 387-390

SUMMARY OF THE INVENTION

Problem to be Solved by the Invention

However, in the noncontact power supply system using the magnetic field resonance system shown in Patent Document 2 or the like, it is required to have functions of adjusting the distance constant and adjusting the angle constant between the power transmission side coil and the power reception side coil. Thus, an external device such as a power transmission side device located outside the human body becomes complex and high level control such as the positional relation and the adjustment of the angle between the coils should be continuously performed. Therefore, a load of a controller of the power transmission side device located outside the human body is large. Furthermore, the high level control should be stopped when replacing the battery.

The present invention is made for solving the above described problems and aims for providing a wireless power supply system capable of wirelessly supplying an electric power to the artificial device installed inside the human body without requiring the adjustment of the position and the angle between the power transmission side coil and the power reception side coil and without interruption of the electric power even when the position and the angle between the power transmission side coil and the power reception side coil are displaced to a certain degree.

Means for Solving the Problem

In order to solve the above described problems, the present invention is a wireless power supply system, including: an internal device installed inside a human body for driving an artificial device installed inside the human body; and an external device installed outside the human body, wherein an electric power is configured to be supplied from the external device to the internal device in a noncontact manner using Parity-Time symmetry, an external power source is connected to the external device, an inverter circuit is provided in the external device for converting a DC voltage supplied from the external power source into an AC voltage, a power transmission side resonance circuit and a power transmission side coil are provided in the external device for converting the AC voltage converted by the inverter circuit into an AC magnetic field and transmitting the electric power to the internal device, a power reception side coil and a power reception side resonance circuit are provided in the internal device for interlinking the AC magnetic field generated in the power transmission side coil, a rectifier circuit is provided in the internal device for converting the AC voltage outputted from the power reception side coil and the power reception side resonance circuit into the DC voltage, the artificial device is configured to be driven by DC power converted by the rectifier circuit, the power transmission side resonance circuit is formed by connecting the power transmission side coil and a power transmission side resonance capacitor in series with each other and connecting the power transmission side coil and the power transmission side resonance capacitor with the inverter circuit, the power reception side resonance circuit is formed by connecting the power reception side coil with at least one of power reception side resonance capacitors, and resonance frequencies are matched with each other between the power transmission side resonance circuit and the power reception side resonance circuit.

Effect of the Invention

According to the wireless power supply system of the present invention, since the wireless power supply utilizes the PT symmetry, the adjustment of the position and the angle are not required between the power transmission side coil and the power reception side coil for supplying the electricity to the artificial device installed inside the human body. Even when the positional relation between the power transmission side coil and the power reception side coil is displaced to a certain degree, the power supply is not interrupted and high transmission efficiency can be maintained. Therefore, the electric power can be continuously supplied in a wireless manner. Furthermore, since the physical phenomenon of the PT symmetry is utilized for the power control, the configurations of the external device and the internal device are simplified.

BRIEF DESCRIPTION OF DRAWINGS

FIGS. 5A, 5B and 5C are schematic diagrams showing circuits of the wireless power supply system for supplying the electric power to the ventricular assist device (artificial device) using the PT symmetry in the first embodiment of the present invention.

MODES FOR CARRYING OUT THE INVENTION

The present invention relates to a wireless power supply system used for an artificial device (implantable medical device) such as artificial heart installed inside a human body.

Hereafter, the embodiments of the present invention will be explained in detail with reference to the drawings.

Figure 1:
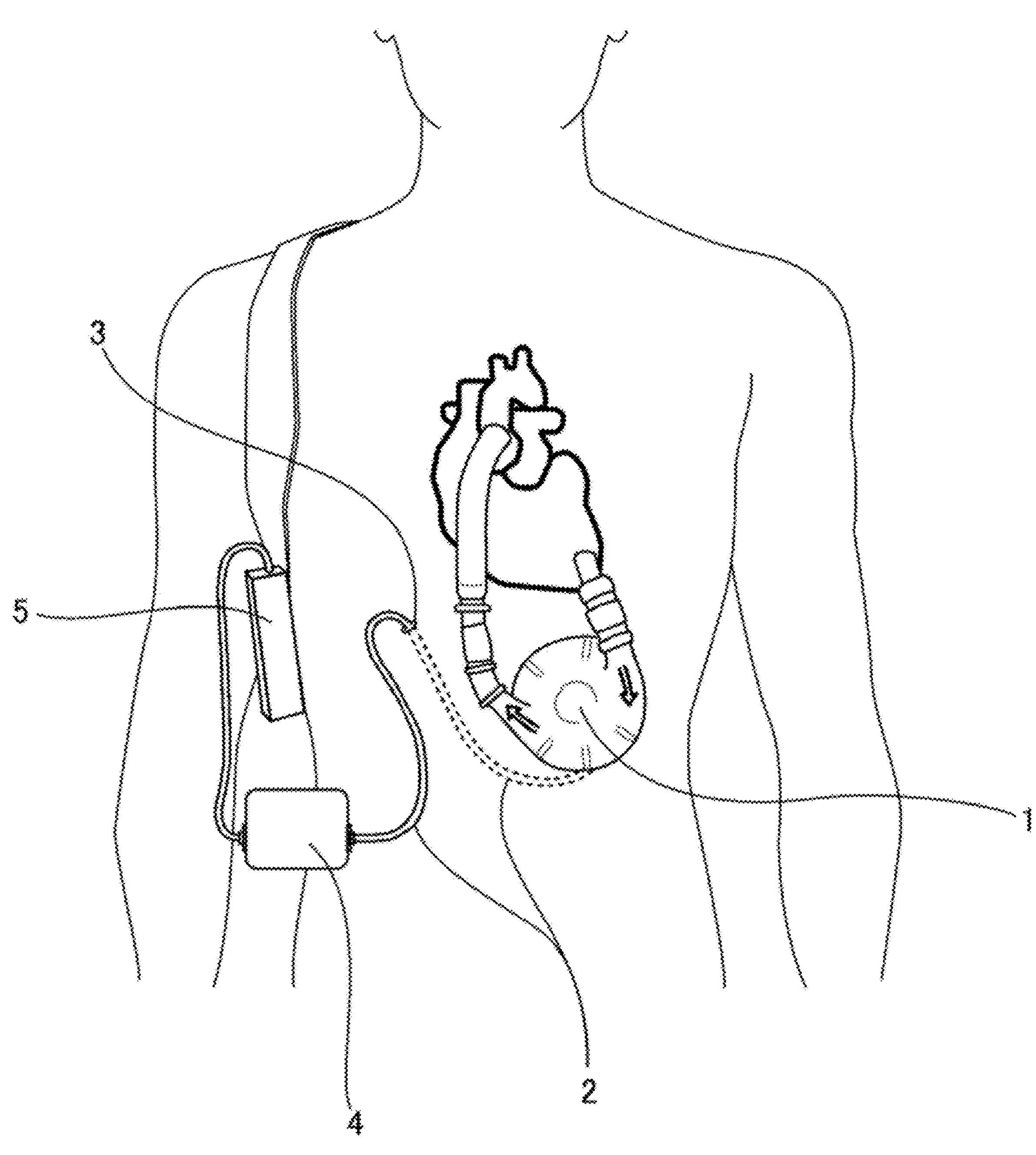
FIG. 1 is a schematic diagram showing a method for supplying an electric power to a ventricular assist device to which the electric power is supplied by a conventional wired communication.

FIG. 1 is a schematic diagram showing a method for supplying an electric power to a ventricular assist device to which an electric power is supplied by a conventional wired communication. The ventricular assist device is a device for assisting blood circulation by attaching a motor-driven pump under the actual heart. FIG. 1 shows a state that a cable 2 such as an electric wire is connected to a ventricular assist device 1 (shown by solid lines) installed inside a human body, the cable 2 is drawn out of the human body from a hole 3 formed on an abdomen of the human body, and the cable 2 is connected to an external controller 4 connected to an external power source (power source installed outside the human body) 5. Here, the cable 2 such as the electric wire located inside the human body is shown by broken lines while the electric wire located outside the human body is shown by solid lines. It can be understood that the cable 2 is drawn outside of the human body from the hole 3 formed on the abdomen.

Currently, the ventricular assist device 1 shown in FIG. 1 is put into practical use for attaching a motor-driven pump (electric pump) under the heart of the patient to assist the blood circulation. In this case, as for the electric power for driving the electric pump, it is common that the hole 3 is formed on the abdomen (human body), the cable 2 such as the electric wire is drawn out of the human body, and the electric wire is connected to the external power source 5 and the controller (controller for driving the electric pump) 4 for driving the ventricular assist device 1.

However, since the hole 3 through which the cable 2 such as the electric wire penetrates is formed on the abdomen (human body), various problems exist. For example, the patient cannot take baths or a risk of infection increases. Thus, there is a demand for applying the wireless power supply technology to the ventricular assist device 1 installed inside the human body to make the electricity flow (supply the electric power) in a non-contact manner.

If the patient is an adult, it is possible to personally care the hole 3 through which the cable 2 such as the electric wire for the ventricular assist device 1 installed inside the human body penetrates or possible to act while caring the hole 3. However, if the patient is a child, special attention needs to be paid for handling the hole 3 and a risk of infection or the like is higher. Therefore, it is more strongly desired to apply the wireless power supply technology to the ventricular assist device 1 to make the electricity flow (supply the electric power) in a non-contact manner without forming the hole 3 on the abdomen (human body).

On the other hand, as for the wireless power supply technology, several technologies such as an electromagnetic induction system and a magnetic field resonance system conventionally exist. In the conventional technologies, the wireless power supply technology of the electromagnetic induction system is used, for example, for charging a mobile phone where coils are vertically arranged. Namely, the electric power can be transmitted only when the distance (transmission distance) between the power transmission side coil and the power reception side coil is extremely close.

However, in the wireless power supply technology of the electromagnetic induction system, since the transmission distance is short (several millimeters), it is impossible to keep the distance between the power transmission side coil and the power reception side coil large. In addition, the charging and the power transmissions become impossible if the power transmission side coil and the power reception side coil are even slightly displaced (misaligned) or separated. Namely, this technology is vulnerable to the position displacement (position misalignment). It is difficult to apply the wireless power supply technology of the electromagnetic induction system to the artificial device such as the artificial heart 1 installed inside the human body.

Furthermore, in the wireless power supply technology of the magnetic field resonance system, since the transmission distance is larger (several centimeters to several meters), the distance between the power transmission side coil and the power reception side coil can be kept larger compared to the electromagnetic induction system. Thus, the wireless power supply technology of the magnetic field resonance system is at a level close to practical application. However, the electricity cannot be transmitted unless the distance between the power transmission side coil and the power reception side coil is fixed constant. The transmission efficiency deteriorates and the required electricity cannot be transmitted if the distance decreases, the distance increases or the angles are different. Due to the above described sensitivity (i.e., vulnerable to the position displacement), it is also difficult to apply the wireless power supply technology of the magnetic field resonance system to the artificial device such as the ventricular assist device 1 installed inside the human body.

Figure 2:
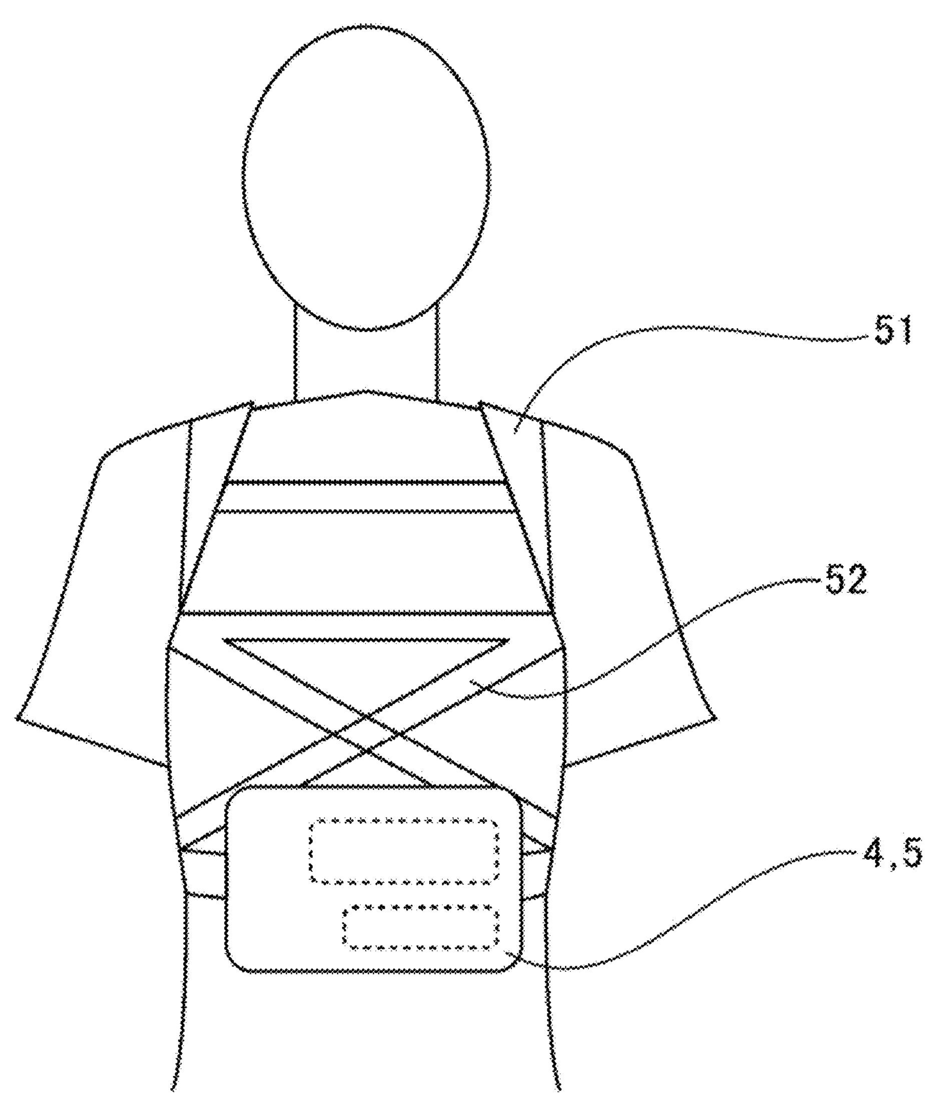
FIG. 2 is a schematic diagram showing a method for attaching an external device to the human body in a conventional wireless power supply system for supplying the electric power to the ventricular assist device using an electromagnetic induction system or a magnetic field resonance system.

Therefore, the wireless power supply system of the magnetic field resonance system cannot be currently used for the ventricular assist device unless the controller 4 (i.e., the external device) connected to the external power source 5 or provided internally with the external power source 5 is tightly fixed by a shoulder belt 51 or a crossbody belt 52 as shown in FIG. 2 so that the distance and the angle between the power transmission side coil located in the controller 4 outside the human body and the power reception side coil (not-illustrated) located near the ventricular assist device inside the human body are not changed (displaced) even when the patient moves. FIG. 2 is a schematic diagram showing a method for attaching an external device to the human body in a conventional wireless power supply system for supplying the electric power to the ventricular assist device using an electromagnetic induction system or a magnetic field resonance system.

However, even when the controller 4 outside the human body is tightly fixed to the human body using the shoulder belt 51, the crossbody belt 52 or the like as shown in FIG. 2 to keep the distance and the angle between the power transmission side coil and the power reception side coil constant, the position may be vertically displaced by several centimeters due to the movement of the human body. In addition, there is a problem of causing heat rash under the belt in summer. Furthermore, it is difficult to replace the battery for supplying the electric power to the external device when the battery is exhausted. Thus, the usage is allowed only under the quite restrictive conditions and usability is not good.

Patent Document 2 discloses the wireless power supply system provided with the controller having the function of adjusting the positional relation and the angle between the power transmission side coil and the power reception side coil to stably supply the electric power to the ventricular assist device or the like in the wireless power supply technology of the magnetic field resonance system. Consequently, even when the position is vertically displaced by several centimeters due to the movement of the human body, the position can be adjusted each time by changing the parameters using the controller in accordance with the position displacement.

However, in the above described system, since the function of adjusting the distance and the angle between the power transmission side coil and the power reception side coil constantly is required, the controller (external device such as power transmission side device) located outside the human body becomes complex. In addition, since the high level control such as the adjustment of the positional relation and the angle between the coils should be continued, a load of the controller (external device such as power transmission side device) located outside the human body is large. Furthermore, when the battery for supplying the electric power to the external device is replaced, the above described high-level control should be stopped.

Therefore, it is desired that a wireless power supply system capable of wirelessly supplying an electric power to the artificial device such as the ventricular assist device installed inside the human body without requiring the adjustment of the position and the angle between the power transmission side coil and the power reception side coil without interruption even when the position and the angle between the power transmission side coil and the power reception side coil are displaced to a certain degree.

Although the experiment and verification are repeated for various wireless power supply systems, no system suitable for practical application is not found.

Here, a wireless power supply technology using Parity-Time symmetry (hereafter, referred to as "PT symmetry") exists as one of the wireless power supply systems. In the wireless power supply system using the PT symmetry, even when the transmission distance is changed or the positional relation between the power transmission side coil and the power reception side coil is displaced, the transmission power is kept constant as long as the PT symmetry is preserved. Namely, in the wireless power supply system using the PT symmetry, the AC power source in the wireless power supply technology of the conventional magnetic field resonance system is replaced with an inverter that behaves electrically similar to a negative resistor (i.e., inverter that behaves as a negative resistor).

The above described technology is known technology as disclosed in Patent Document 3, for example. More specifically, the inverter that behaves as the negative resistor is the inverter whose switching frequency and voltage amplitude are not fixed in advance. The inverter has a circuit configuration where the switching frequency is determined by an apparent resonance frequency of a wireless power supply circuit seen from the output terminal of the inverter. The switching frequency of the inverter follows the change of the apparent resonance frequency of the wireless power supply circuit that may vary depending on the transmission distance and the position displacement of the coils with fast response speed. Here, the wireless power supply circuit refers to the circuits including the power transmission side resonance circuit, the power reception side resonance circuit and all following circuits connected to them. The apparent resonance frequency refers to the substantial resonance frequency where the interaction between the power transmission side resonance circuit and the power reception side resonance circuit is taken into account since they interact with each other.

However, the conventional wireless power supply system using the PT symmetry is driven by a high frequency of approximately 1 to 3 MHz and air-core coils are used for the power transmission side coil and the power reception side coil. Thus, the dimension of the coils should be large and the application to be adopted is limited. Specifically, the dimension of the coil is approximately 60 cm in diameter in the conventional wireless power supply system using the PT symmetry (shown in Non-patent Document 1). Furthermore, since the frequency is high, if a metal object (conductive object) is placed around the power transmission side coil and the power reception side coil, the transmission efficiency deteriorates due to the eddy current loss in the conductive object. Therefore, it is impossible to apply the above described technology to the artificial device such as the ventricular assist device installed inside the human body.

In order to solve the problems of the conventional wireless power supply system using the PT symmetry, one of the inventors of the present invention invented a wireless power supply device using the PT symmetry capable of reducing the deterioration of the transmission efficiency even when a metal object is placed around the coils, capable of keeping high transmission efficiency even when the transmission distance is changed or the positions of the coils are displaced, capable of downsizing the power transmission side coil and the power reception side coil, and applicable to various applications by using low frequency of 100 kHz or less and filed a patent application in 2021 (shown in Patent Document 3).

The present invention is achieved through repeated experiments and trial and error for applying the wireless power supply device using the PT symmetry described in Patent Document 3 which is the prior application to the wireless power supply system for supplying the electric power to the artificial device such as the ventricular assist device installed inside the human body.

First Embodiment

The wireless power supply system for supplying the electric power to the ventricular assist device using the PT symmetry concerning the first embodiment of the present invention is the wireless power supply system using the PT symmetry including: an internal device installed inside a human body for driving an artificial device installed inside the human body; and an external device installed outside the human body, wherein an electric power is configured to be supplied from the external device to the internal device in a noncontact manner. Since the wireless power supply system utilizes the PT symmetry, the electric power can be wirelessly transmitted from the outside of the human body to the artificial device installed inside the human body without forming the hole on the human body and without connecting the electric wire. Thus, a risk of infection of the patient can be eliminated and excellent effect can be obtained. In the first embodiment, the artificial device is explained using the ventricular assist device as an example.

Figure 3:
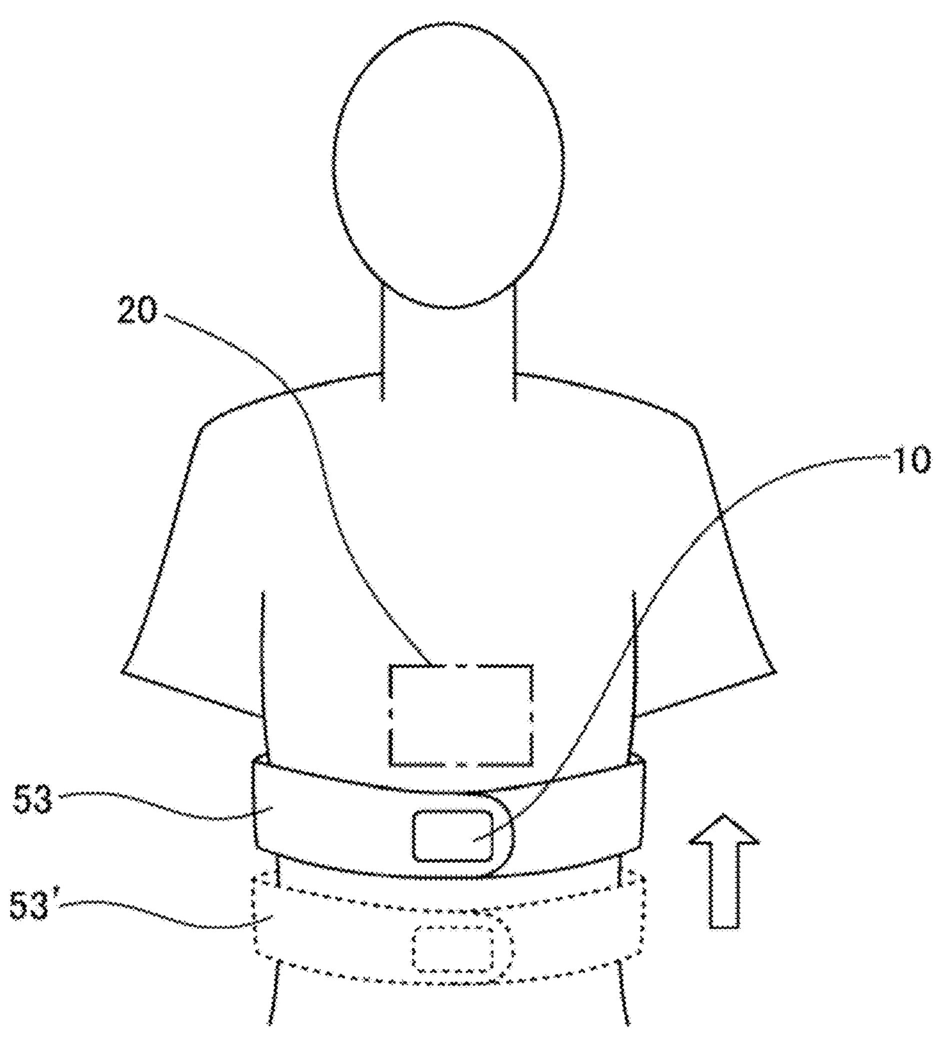
FIG. 3 is a schematic diagram showing a method for attaching an external device to a human body in a wireless power supply system for supplying the electric power to the ventricular assist device (artificial device) using the PT symmetry in the first embodiment of the present invention.
Figure 4:
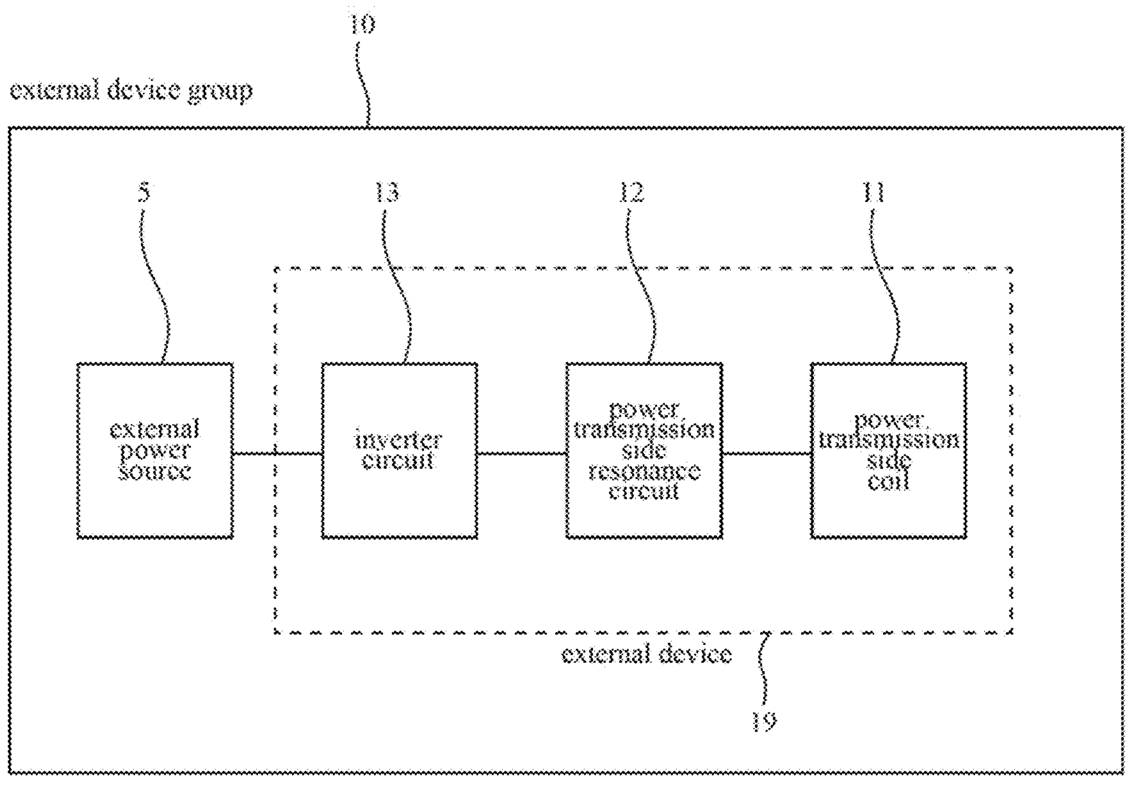
FIG. 4 is an explanation drawing showing a schematic configuration of an external device and an internal device for driving the ventricular assist device in the wireless power supply system for supplying the electric power to the ventricular assist device (artificial device) using the PT symmetry in the first embodiment of the present invention.
Figure 4:
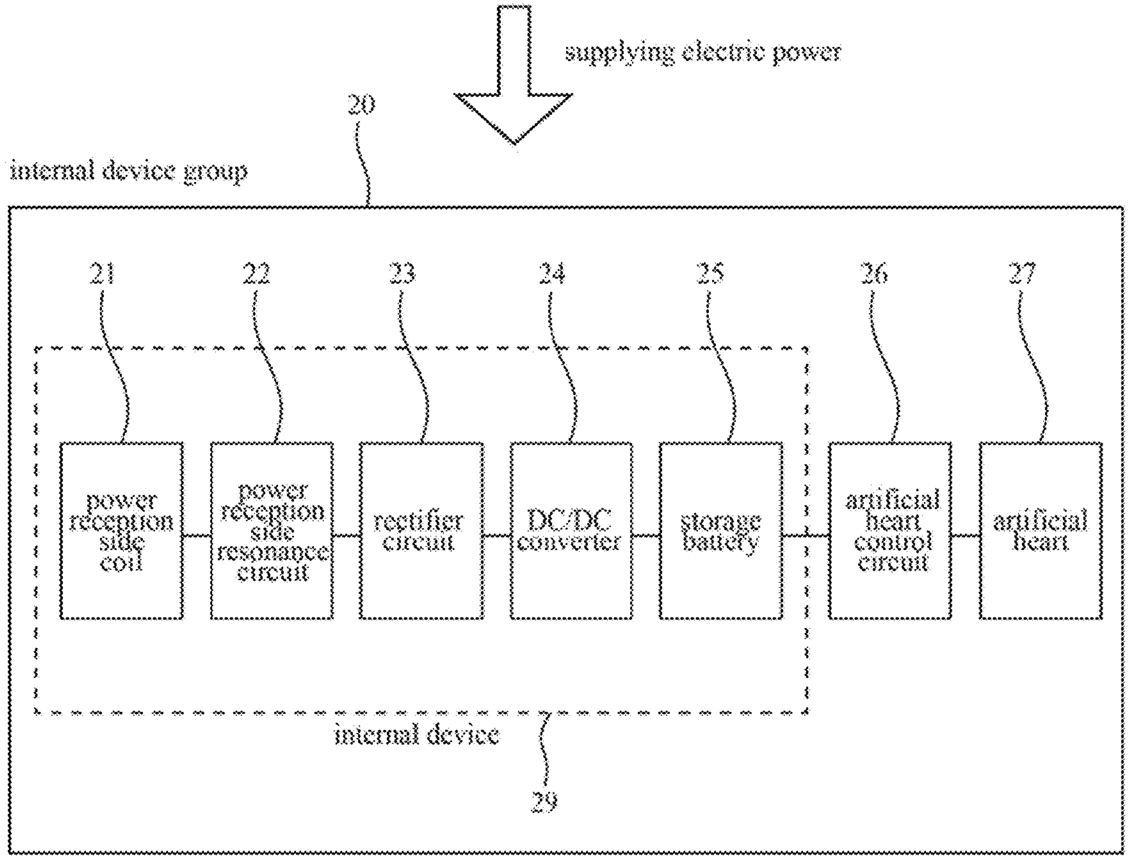
Figure 5B:
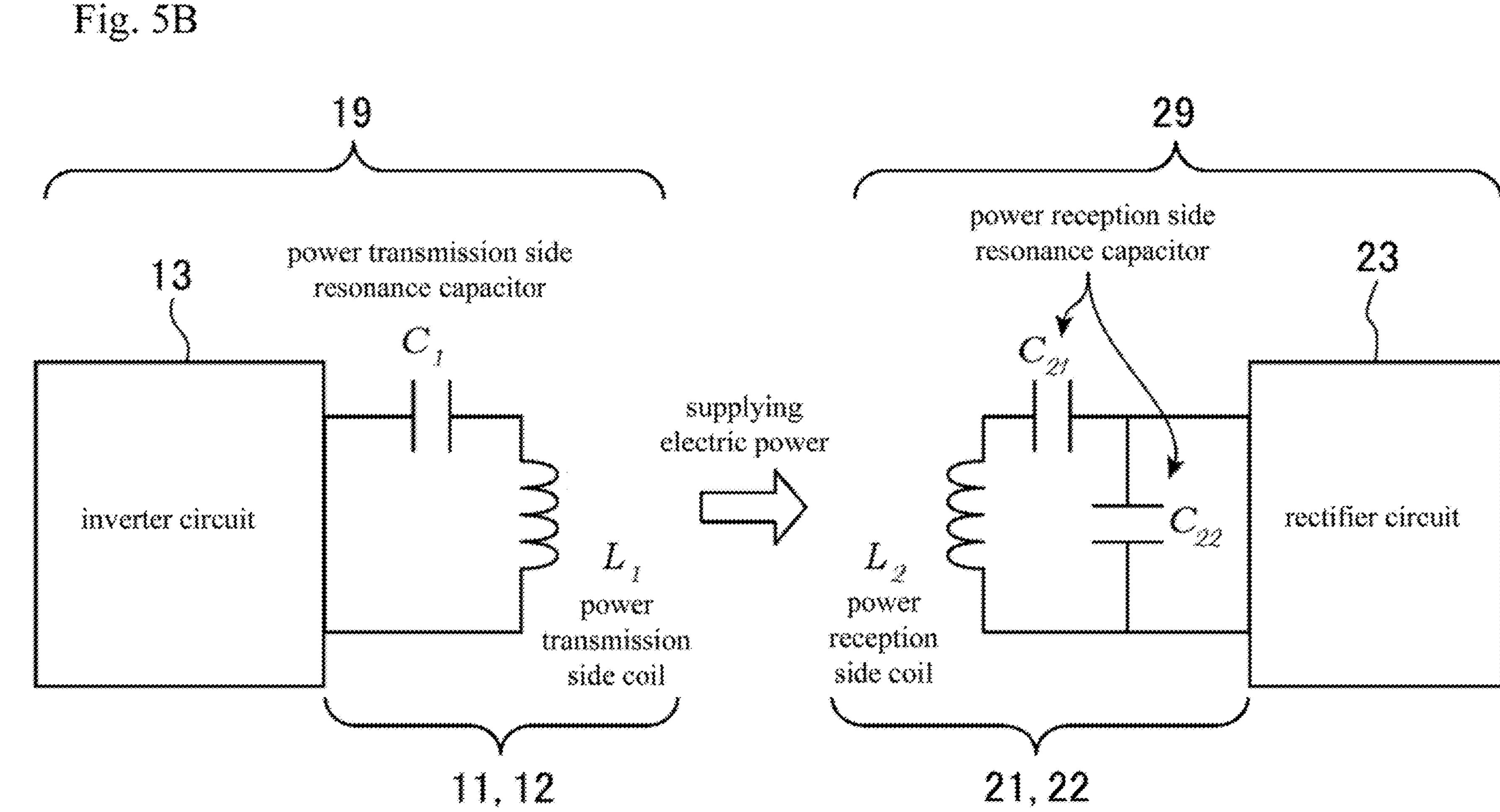
Figure 5C:
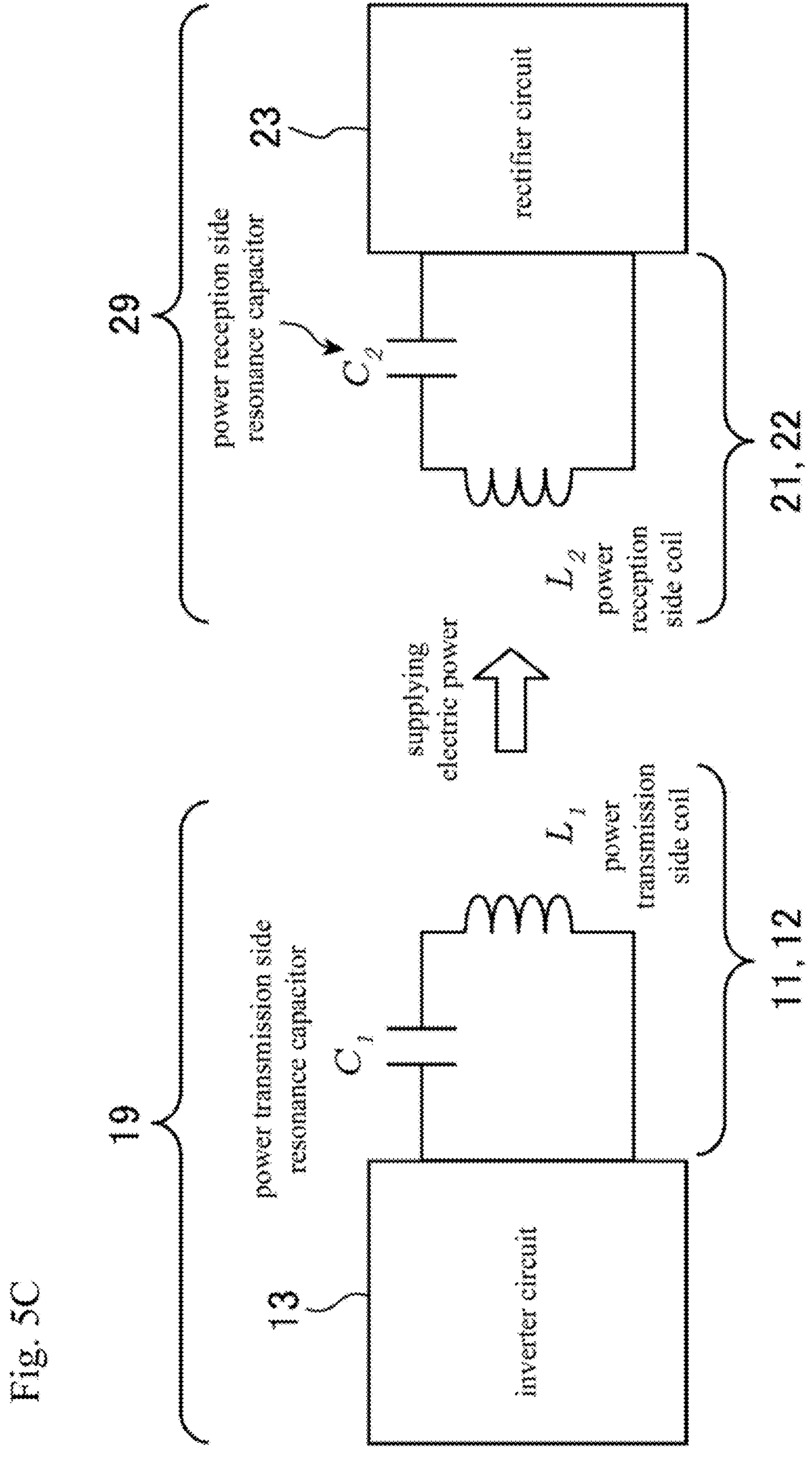

FIG. 3 is a schematic diagram showing a method for attaching the external device to the human body in the wireless power supply system for supplying the electric power to the ventricular assist device (artificial device) using the PT symmetry in the first embodiment of the present invention. Here, the method for attaching an external device group 10 including an external device 19 (shown in FIG. 4) is shown. FIG. 4 is an explanation drawing showing a schematic configuration of the external device 19 and an internal device 29 for driving the ventricular assist device (artificial heart control circuit 26 and artificial heart 27) in the wireless power supply system for supplying the electric power to the ventricular assist device (artificial device) using the PT symmetry in the first embodiment of the present invention. FIGS. 5A, 5B and 5C are schematic diagrams showing circuits of the wireless power supply system for supplying the electric power to the ventricular assist device (artificial device) using the PT symmetry in the first embodiment of the present invention.

In FIG. 3, an internal device group 20 (shown in FIG. 4) is schematically shown by dash-dotted line in a state that the external device group 10 installed outside the human body is attached around the waist of the human body (patient) by a waist belt 53 for supplying the electric power to the internal device group 20 in a noncontact manner. As shown inf FIG. 3, it is enough if the external device group 10 is attached to the waist belt 53 such as an ordinarily trouser belt in the first embodiment of the present invention different from the method for attaching the external device (e.g., controller 4) to the human body shown in FIG. 2 in the wireless power supply system of the ventricular assist device of the conventional magnetic field resonance system where the controller 4 located outside the human body is tightly fixed to the human body using the shoulder belt 51 or the crossbody belt 52.

In addition, FIG. 4 shows a schematic configuration of the entire wireless power supply system for the ventricular assist device (the artificial device) using the PT symmetry concerning the first embodiment of the present invention. As shown in FIG. 4, the wireless power supply system of the first embodiment comprises the external device group 10 including the external device 19 installed outside the human body and the internal device group 20 including the internal device 29 installed inside the human body. The external device 19 is equipped with an inverter circuit 13 and a power transmission side resonance circuit 12 and a power transmission side coil 11. Here, the external device group 10 is configured to include the external power source 5.

The external power source 5 is configured to supply the electric power to the inverter circuit 13. The external power source 5 can be any power source that outputs a DC (direct current) voltage. Specifically, the external power source 5 can be a battery or a device for converting a commercial power source (100 V, 50 Hz or 60 Hz) supplied from a wall outlet such as an AC adapter into the DC voltage. Note that the explanation will be made in condition that the external power source 5 is a battery and the battery is built in the external device group 10. However, the battery is not necessarily installed inside the external device group 10. For example, the battery connected to the external device 19 can be carried on the back of the human body or the commercial power source supplied from the wall outlet can be used.

The inverter circuit 13 is the device for converting the DC voltage supplied from the external power source 5 to an AC (alternating current) voltage. The inverter circuit 13 is the inverter that behaves electrically similar to a negative resistor. The detailed explanation of the inverter that behaves electrically similar to the negative resistor is omitted since this is previously described. The power transmission side resonance circuit 12 and the power transmission side coil 11 will be explained later with reference to FIGS. 5A, 5B and 5C. In the inverter circuit 13, the power transmission side resonance circuit 12 is required when the AC voltage converted from the DC voltage is transmitted to the power transmission side coil 11. Namely, the inverter circuit 13 is configured so that the relation between the output current and the output voltage of the inverter circuit 13 is similar to the relation between the current and the voltage of the negative resistor. When the power transmission side resonance circuit 12 and the inverter circuit 13 are connected to each other, oscillation phenomenon is generated. Note that the detailed explanation of the oscillation phenomenon is omitted since the oscillation phenomenon is conventionally known technology.

As described above, the electric power (DC voltage) supplied from the external power source 5 incorporated in the external device group 10 is converted into the AC voltage by the inverter circuit 13 in the external device 19 and the AC voltage is converted into an AC magnetic field through the power transmission side resonance circuit 12 and the power transmission side coil 11. Thus, the electric power is transmitted without contacting with a power reception side coil 21.

As described above, the external device 19 installed outside the human body is provided with the inverter circuit 13 connected to the external power source 5 for converting the DC voltage supplied from the external power source 5 into the AC voltage, and the power transmission side resonance circuit 12 and the power transmission side coil 11 for converting the AC voltage converted by the inverter circuit 13 into an AC magnetic field and transmitting the electric power to the internal device 29. The external device group 10 internally equipped with the external device 19 and the external power source 5 is small and lightweight so that the external device group 10 can be attached to the waist belt 53 such as an ordinarily trouser belt shown in FIG. 3.

In addition, the internal device group 20 including the ventricular assist device (artificial heart control circuit 26 and artificial heart 27) is installed inside the human body and directly attached to the heart of the human. As shown in FIG. 4, the internal device 29 is equipped with a power reception side coil 21, a power reception side resonance circuit 22, a rectifier circuit 23, a DC/DC converter 24 and a storage battery 25. The above described components of the internal device 29 are connected to the ventricular assist device comprised of the artificial heart control circuit 26 and the artificial heart 27 and the electric power transmitted from the external device 19 is supplied to the ventricular assist device.

Note that the detailed explanation of the ventricular assist device (artificial heart control circuit 26 and artificial heart 27) is omitted since the ventricular assist device is conventionally known device. The artificial heart 27 includes a liquid feed pump for circulating the blood inside the artificial heart 27. The artificial heart control circuit 26 is a control circuit for controlling the flow rate of the liquid feed pump.

The power reception side coil 21 and the power reception side resonance circuit 22 will be also explained later with reference to FIGS. 5A, 5B and 5C. The power reception side resonance circuit 22 and the power reception side coil 21 located inside the internal device 29 installed inside the human body are required as a set similar to the fact that the power transmission side coil 11 and the power transmission side resonance circuit 12 are required for the external device 19 of the power transmission side. The power reception side coil 21 and the power reception side resonance circuit 22 are connected to each other.

When the electric power (AC magnetic field) from the external device 19 is transmitted from the power transmission side coil 11 to the power reception side coil 21 in a noncontact manner, the rectifier circuit 23 converts the electric power (AC voltage) outputted from the power reception side coil 21 and the power reception side resonance circuit 22 for interlinking the AC magnetic field generated from the power transmission side coil 11 into the DC voltage. At this time, when using the electric power, it is preferred to adjust the electric power to a predetermined voltage such as 24 V or 12 V for driving the pump and the motor at the predetermined voltage.

Therefore, the DC/DC converter 24 adjusts the DC electric power (DC voltage) converted by the rectifier circuit 23 to the predetermined voltage fitted to a purpose. In addition, the voltage value received by the DC/DC converter 24 varies to a certain extent depending on the change of the transmission distance, for example. Since the voltage fluctuation adversely affects the pump and the rotation speed of the motor, the fluctuation of the voltage value needs to be suppressed by some method. The DC/DC converter 24 also has the function of suppressing the fluctuation of the voltage value for supplying a stable voltage to the pump and the motor. Note that the DC/DC converter 24 can be any general DC/DC converter since general DC/DC converter has the above described function.

Furthermore, the internal device 29 of the first embodiment is equipped with a storage battery 25. Thus, the AC voltage received from the external device 19 is converted into the DC voltage, the DC voltage is adjusted to the predetermined voltage by the DC/DC converter 24, and the electric power adjusted to the predetermined value can be temporarily stored (preserved) in the storage battery 25. When the artificial device is the ventricular assist device (artificial heart control circuit 26 and artificial heart 27) as shown in the first embodiment, there is a risk of cardiac arrest and a risk of death if the supply of the electric power is interrupted even for a moment due to some accident and malfunction of the external device 19 of the power transmission side or the replacement of the buttery for supplying the electric power to the external device 19. Thus, it is assumed that a small storage battery capable of driving the artificial device only for five minutes or ten minutes, for example, is incorporated for the case where the above described problem occurs.

Namely, although the storage battery 25 is required for applying the wireless power supply system to the artificial heart, it is not necessary to provide the storage battery 25 depending on the artificial device to be used. When the internal device 29 does not include the storage battery 25, the ventricular assist device (artificial heart control circuit 26 and artificial heart 27) can be driven by the electric power at the voltage value outputted from the DC/DC converter 24.

As described above, it is preferable to provide the DC/DC converter 24 for adjusting the DC voltage converted by the rectifier circuit 23 to the predetermined voltage value and stably outputting the DC voltage. However, it is not necessary to provide the DC/DC converter. When the internal device 29 does not include the DC/DC converter 24, the storage battery 25 can temporarily store the DC electric power converted by the rectifier circuit 23. When the internal device 29 includes neither the DC/DC converter 24 nor the storage battery 25, it is possible to drive the ventricular assist device (artificial heart control circuit 26 and artificial heart 27) by the DC electric power converted by the rectifier circuit 23.

As described above, the internal device 29 is equipped with at least: the power reception side coil 21 and the power reception side resonance circuit 22 for interlinking the AC magnetic field generated from the power transmission side coil 11; and the rectifier circuit 23 for converting the AC voltage outputted from the power reception side coil 21 and the power reception side resonance circuit 22 into the DC voltage, wherein the ventricular assist device (artificial heart control circuit 26 and artificial heart 27) is driven by the DC electric power converted by the rectifier circuit 23. In addition, the internal device 29 is equipped with the storage battery 25 for storing the DC electric power converted by the rectifier circuit 23. The ventricular assist device (artificial heart control circuit 26 and artificial heart 27) can be driven by the electric power stored in the storage battery 25.

As described above, the electric power (DC voltage) transmitted from the external power source 5 incorporated in the external device group 10 is converted into the AC voltage by the inverter circuit 13 in the external device 19, the AC voltage is converted into the AC magnetic field through the power transmission side resonance circuit 12 and the power transmission side coil 11, and the electric power is transmitted to the power reception side coil 21 in a noncontact manner. Consequently, the electric power is supplied to the ventricular assist device (artificial heart control circuit 26 and artificial heart 27) and the ventricular assist device drives the pump for assisting the blood circulation of the actual heart. Here, the power reception side coil 21 installed inside the human body can be installed at any place as long as the power reception side coil 21 can be installed in a state of being connected to the other devices in the internal device 29. It is natural to install the power reception side coil 21 around the navel near the internal device group 20 since there is an available space near the heart and the place where the ventricular assist device is installed in the human body.

The circuit diagram comprising the power transmission side coil 11, the power transmission side resonance circuit 12 and the inverter circuit 13 shown in FIG. 4 is the left half of FIGS. 5A, 5B and 5C. The circuit diagram comprising the power reception side coil 21, the power reception side resonance circuit 22 and the rectifier circuit 23 shown in FIG. 4 is the right half of FIGS. 5A, 5B and 5C. Namely, the left half of FIGS. 5A, 5B and 5C shows the circuit diagram of the external device 19 (circuit diagram of the power transmission side resonance circuit 12) while the right half shows the circuit diagram of the internal device 29 (circuit diagram of the power reception side resonance circuit 22).

As shown in FIGS. 5A, 5B and 5C, the power transmission side resonance circuit 12 is formed by connecting the power transmission side coil 11 and a power transmission side resonance capacitor $C_1$ in series with each other and connecting them to the inverter circuit 13. The power reception side resonance circuit 22 is formed by connecting the power reception side coil 21 with at least one of the power reception side resonance capacitors ($C_2$, $C_{21}$, $C_{22}$). It is important to specify the resonance frequencies of the power transmission side resonance circuit 12 and the resonance frequency of the power reception side resonance circuit 22 to match with each other. Namely, it is important that the resonance frequencies of two resonance circuits of the power transmission side and the power reception side are matched with each other.

As for the power reception side resonance circuit 22, in addition to the circuit pattern shown in FIG. 5A where one power reception side resonance capacitors C2 is connected in parallel with the power reception side coil 21, the circuit pattern shown in FIG. 5B where one power reception side resonance capacitor $C_{21}$ is connected in series with the power reception side coil 21 and another power reception side resonance capacitor $C_{22}$ is connected in parallel. Namely, in the cases of FIG. 5A and FIG. 5B, it can be said that the power reception side resonance circuit 22 is formed by connecting the power reception side coil 21 in parallel with at least one of the power reception side resonance capacitors ($C_2$ or $C_{22}$). As another pattern, it is also considered that one power reception side resonance capacitor $C_2$ is connected in series with the power reception side coil 21 as shown in FIG. 5C. Namely, the power reception side resonance circuit 22 is formed by connecting the power reception side coil 21 with at least one of the power reception side resonance capacitors.

Note that the explanation is made for the case where one power reception side resonance capacitor $C_2$ is connected in parallel with the power reception side coil 21 shown in FIG. 5A in the first embodiment of the present invention.

By using the above described circuit, an alternating current (AC) magnetic field is generated from the external device 19 installed outside the human body toward the internal device 29 installed inside the human body. However, when cells or tissues are exposed to high-frequency AC magnetic field, the cells or tissues are heated and damaged. Thus, in case of the wireless power supply for supplying the electric power to the artificial device installed inside the human body, there is a limitation that high frequency cannot be used. As mentioned earlier, the wireless power supply system using the PT symmetry in the prior research is achieved by high frequency of 1 to 3 MHz. Thus, it is difficult to apply this technology to the wireless power supply system for supplying the electric power to the artificial device such as an artificial heart installed inside the human body.

In addition, the energy loss of the AC magnetic field in the conductive object is proportional to the square of the frequency. Namely, if the frequency increases tenfold, the amount of heat generation increases hundredfold. If the frequency increases hundredfold, the amount of heat generation increases ten-thousandfold. Thus, it is very important condition to keep the frequency low. Therefore, the applicant of the present invention aims for reducing the amount of heat generation by more than 100 times compared to the conventional system by setting the frequency 200 kHz or less for reducing the frequency to approximately one-tenth compared to the conventional wireless power supply system using the PT symmetry. The applicant currently conducts experiments at the frequency of approximately 50 kHz.

Furthermore, in the wireless power supply system using the PT symmetry of the prior research, the power transmission side coil and the power reception side coil are realized by an air core coil having a diameter of approximately 60 cm. However, it is almost impossible to install the coil having the above described size inside the human body. Thus, not only the problem of high frequency, in terms of the shape and the size of the coil, it is impossible to apply the conventional technology to the wireless power supply system for supplying the electric power to the artificial device such as an artificial heart installed inside the human body.

Figure 6A:
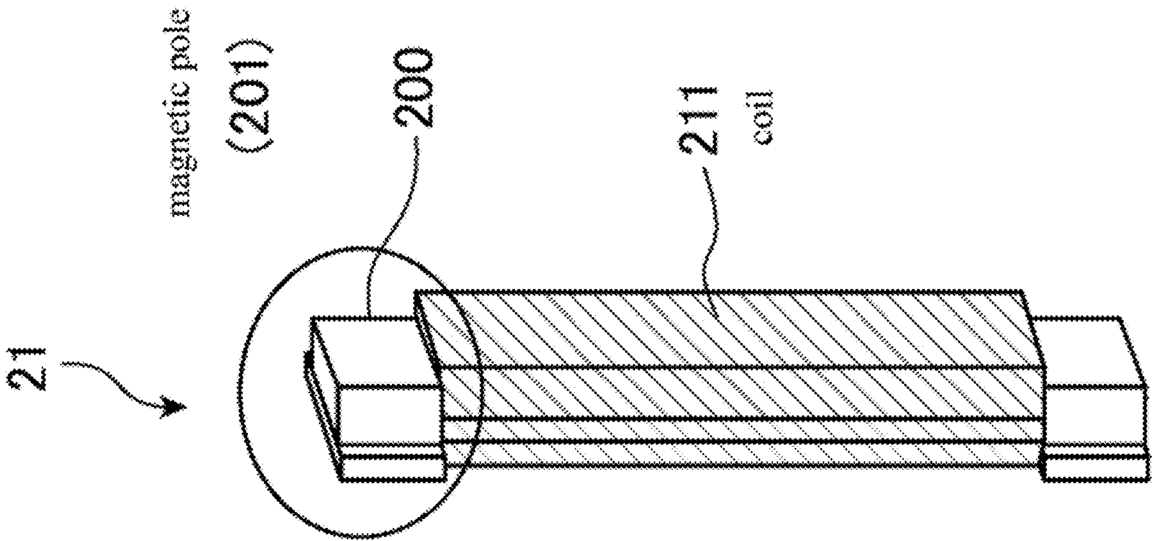
FIGS. 6A and 6B are explanation drawings showing a schematic configuration of the power transmission side coil and the power reception side coil used in the wireless power supply system using the PT symmetry in the first embodiment of the present invention.
Figure 6A:
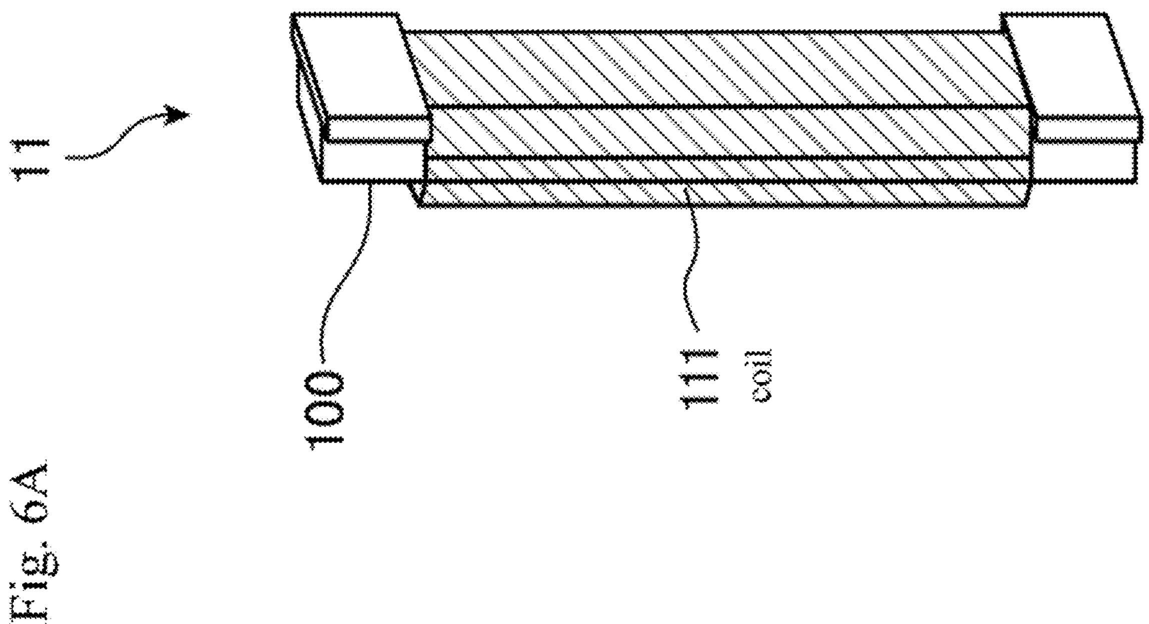
Figure 6B:
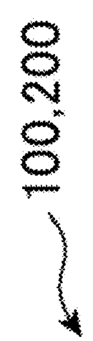
Figure 6B:
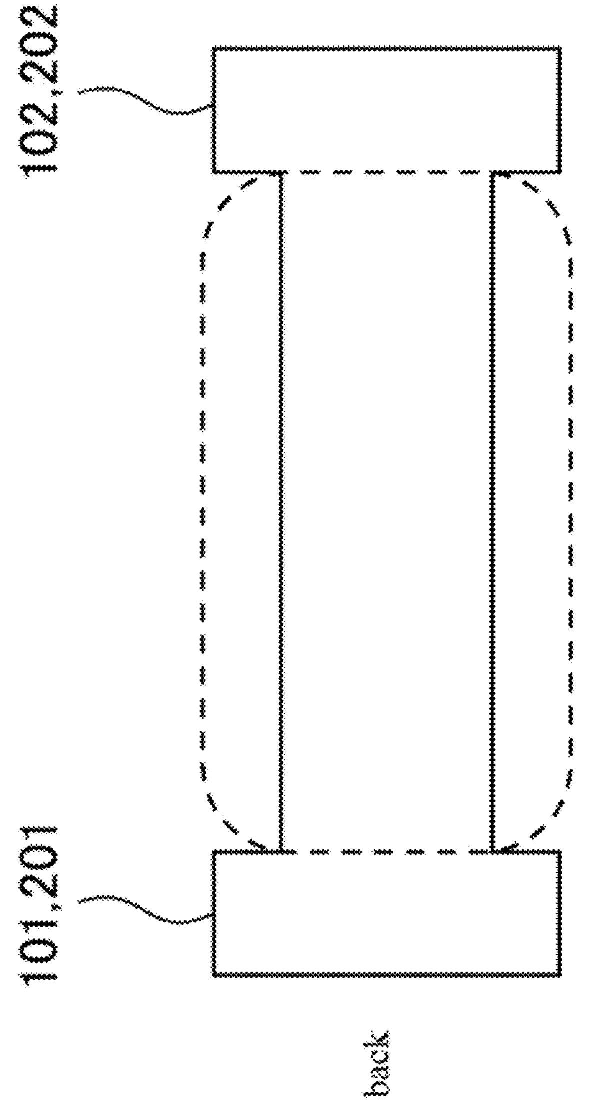
Figure 6B:
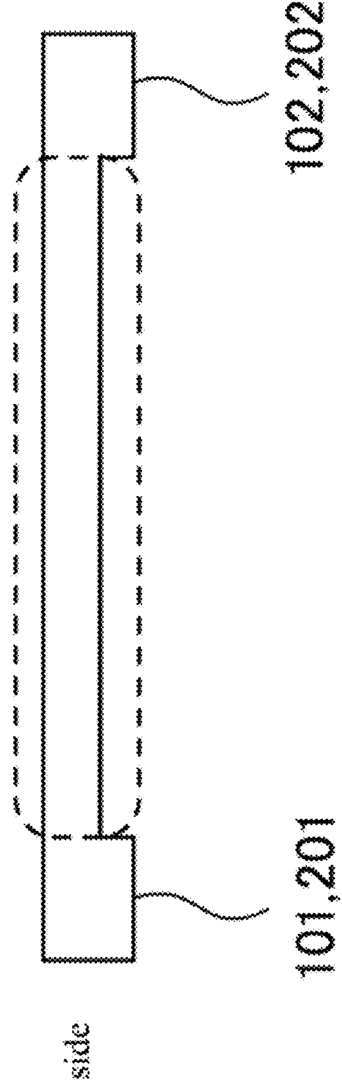

FIGS. 6A and 6B are explanation drawings showing a schematic configuration of the power transmission side coil 11 and the power reception side coil 21 used in the wireless power supply system using the PT symmetry in the first embodiment of the present invention. As shown in FIG. 6A, each of the power transmission side coil 11 and the power reception side coil 21 is a solenoid type coil formed by winding a coil (e.g., litz wire) 111, 211 around a magnetic core 100, 200 made of soft magnetic material such as a ferrite material. As the shape of the coil used for the wireless power supply, a circular spiral-type coil (or pancake-type coil) is used in many cases. The fact that the solenoid type coil is used as the shape of the coil is one of the features of the present invention. The size of the coil can be small by using the solenoid type coil using the soft magnetic material as the core. Thus, it is possible to install the coil inside the human body.

As shown in FIG. 6B, the magnetic core 100 (or 200) includes magnetic poles 101, 102 (or 201, 202) having an approximately rectangular parallelopiped shape where the coil is not wound at both ends of the magnetic core 100 (or 200). Namely, the magnetic poles 101, 102 (or 201, 202) are located at the portion other than the portion where the coil 111 (or 211) is wound (portion surrounded by broken line in FIG. 6B). The magnetic poles 101, 102, 201, 202 are formed so that the area (area of both ends in the upper figure (back) of FIG. 6B) of the facing surface when the power transmission side coil 11 and the power reception side coil 21 face each other is larger than the area of the other surfaces of the magnetic poles. Consequently, the magnetic coupling coefficient when the power transmission side coil 11 and the power reception side coil 21 face each other can be increased. Therefore, the transmission distance of the coils can be extended and the allowance range of the position displacement can be broadened.

Here, the magnetic coupling coefficient between the two coils will be explained. When the positions of two coils are changed (e.g., the distance or the angle between the coils is changed), the magnetic coupling coefficient km between the two coils changes. The magnetic coupling coefficient km between two coils decreases as the transmission distance between the two coils increases, and also decreases when the position displacement between the two coils increases. On the contrary, the magnetic coupling coefficient km increases as the distance between the two coils decreases. The magnetic coupling coefficient km approaches almost 1 when the two coils are brought almost into contact. Namely, the magnetic coupling coefficient km varies within the range of 0 to 1.

Figure 7A:
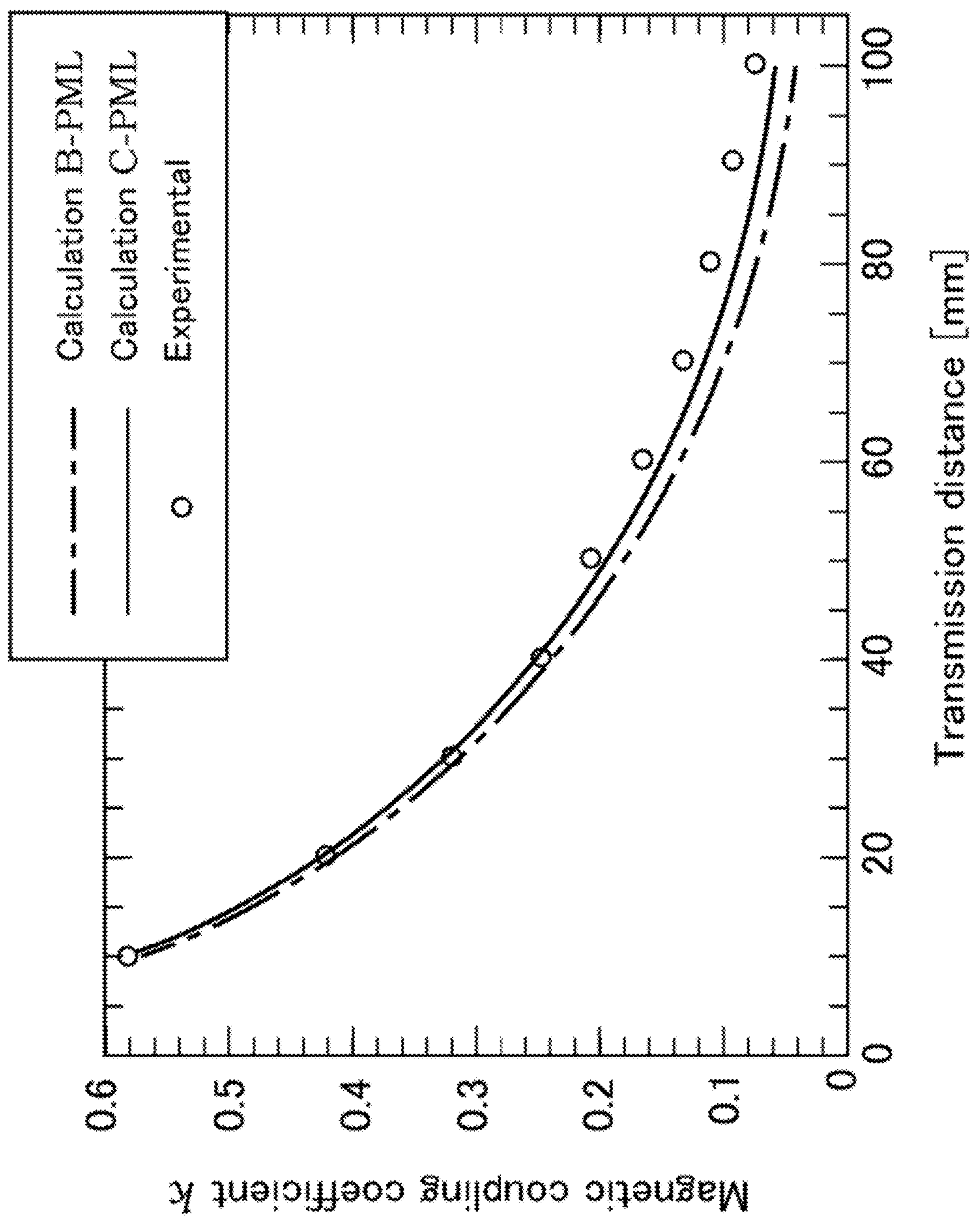
FIGS. 7A and 7B are graphs showing the relation between the positional relation of two coils (power transmission side coil and power reception side coil) and a magnetic coupling coefficient used in the wireless power supply system using the PT symmetry in the first embodiment of the present invention.
Figure 7B:
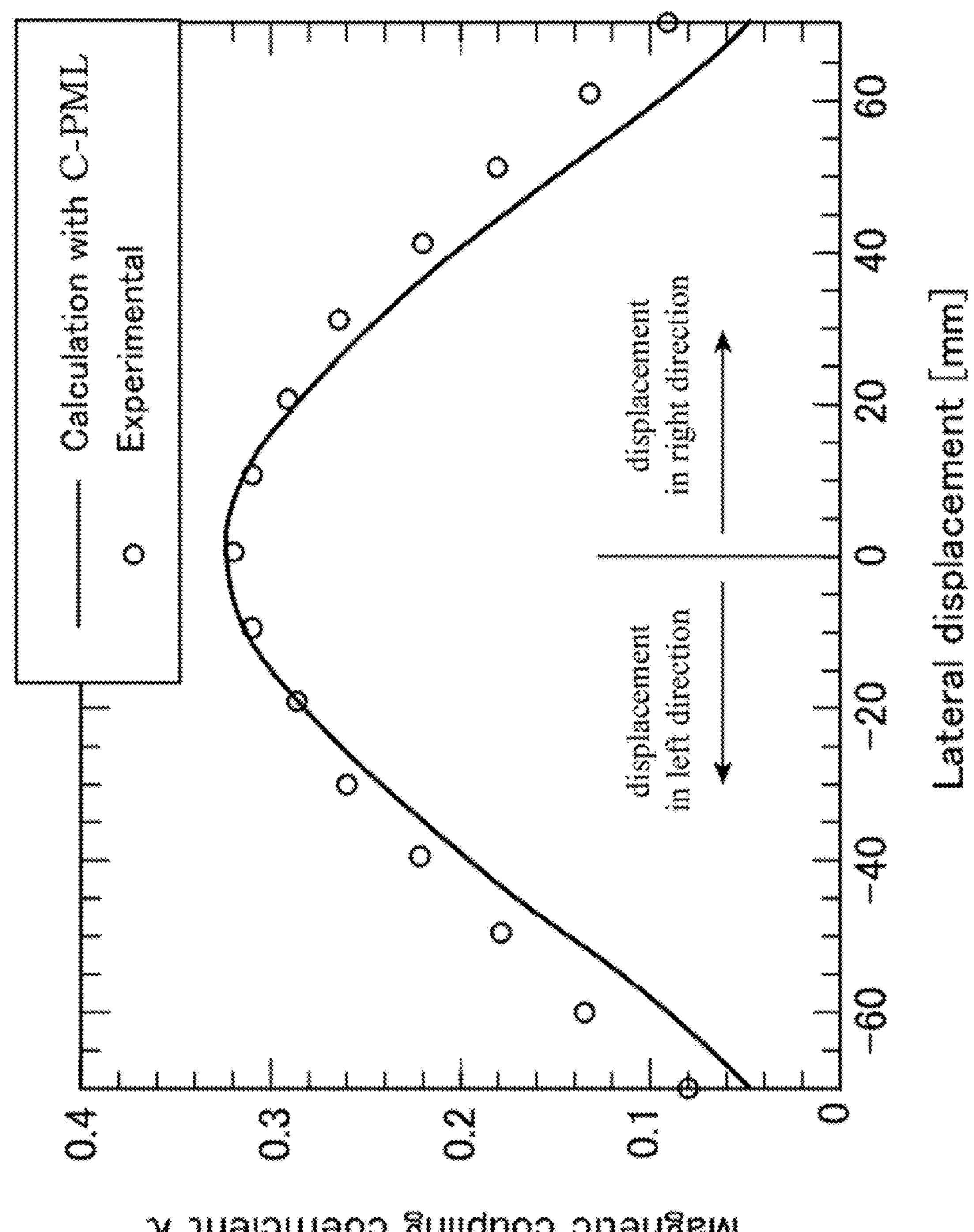

FIGS. 7A and 7B are graphs showing the relation between the positional relation of two coils (power transmission side coil 11 and power reception side coil 21) and the magnetic coupling coefficient used in the wireless power supply system using the PT symmetry in the first embodiment of the present invention. FIG. 7A shows the relation between the transmission distance of the two coils and the magnetic coupling coefficient. FIG. 7B shows the relation between the lateral displacement of the two coils and the magnetic coupling coefficient.

In both FIGS. 7A and 7B, the circles in the graphs indicate the measurement result of the experiment while the solid lines and dash-dotted lines indicate the theoretical calculation values. However, the result of the experiment is an approximately same value as the calculation value. When FIG. 7A is viewed, it can be understood that the magnetic coupling coefficient increases as the transmission distance between the two coils decreases while the magnetic coupling coefficient decreases as the transmission distance increases. When FIG. 7B is viewed, it can be understood that the magnetic coupling coefficient is the largest when the two coils face to each other without being laterally displaced (the position displacement is 0 mm). The magnetic coupling coefficient decreases as the position displacement to the left increases and as the position displacement to the right increases. Although only the lateral displacement is shown here, it can be also understood that the magnetic coupling coefficient also decreases as the displacement in the vertical direction increases or when the rotation direction is displaced.

When the magnetic coupling coefficient becomes smaller than a certain value, the PT symmetry cannot be preserved. Namely, the PT symmetry can be preserved within a certain limit (threshold) of the magnetic coupling coefficient. Therefore, if a critical magnetic coupling coefficient $k_{mC}$, which is the limit value of the magnetic coupling coefficient, can be smaller, the output of the electric power can be stabilized even when the transmission distance between the coils changes or the position is displaced. Namely, the smaller the critical magnetic coupling coefficient, the more PT symmetry can be preserved and more constant the output of the electric power can be supplied even when the distance between the two coils changes or the angle is displaced.

This critical magnetic coupling coefficient $k_{mC}$, which indicates the limit value of the magnetic coupling coefficient, can be expressed by Equation 1.

$$k_{mC} = \frac{1}{Q_2} + \frac{1}{\omega_0 C_2 R_L} \quad \text{[Equation 1]}$$

Here, $Q_2$ in the denominator of the first term is a value (Q value) representing a quality factor of the power reception side coil 21, ω0 in the denominator of the second term is the resonance frequency, $C_2$ is the power reception side resonance capacitor of the power reception side coil 21, and $R_L$ is a resistive load of the wireless power supply system (i.e., equivalent electrical resistance value of the artificial heart including the DC/DC converter in this example). Since Equation 1 described above is the sum of the first and second terms, the value of Equation 1 can be made small if both the first and second terms can be made small. Namely, regarding the first term, since $1/Q_2$ is preferably made small, it can be understood that $Q_2$ should be a large value.

In addition, regarding the resonant frequency ω0, when a self-inductance of the power reception side coil 21 is L2, the resonant frequency ω0 can be expressed by Equation 2. Furthermore, Equation 2 can be transformed into Equation 3, and $C_2$ can be shown in Equation 4. When the power reception side resonance circuit 22 has a circuit pattern where one power reception side resonance capacitor $C_{21}$ is connected in series with the power reception side coil 21 and another power reception side resonance capacitor $C_{22}$ is connected in parallel as shown in FIG. 5B, the relationship $C_2=C_{21}\times C_{22}/(C_{21}+C_{22})$ is established and $C_2$ can be expressed as shown in Equation 4 even in this case. When Equation 4 is substituted for $C_2$ in Equation 1, the critical magnetic coupling coefficient $k_{mC}$ can be expressed as shown in Equation 5. Equation 6 shows only the result of Equation 5.

$$\omega_0 = \frac{1}{\sqrt{C_2 L_2}} \quad \text{[Equation 2]}$$

$$C_2 L_2 = \frac{1}{\omega_0^2} \quad \text{[Equation 3]}$$

$$C_2 = \frac{1}{L_2 \omega_0^2} \quad \text{[Equation 4]}$$

$$k_{mC} = \frac{1}{Q_2} + \frac{1}{\frac{\omega_0}{L_2 \omega_0^2} R_L} = \frac{1}{Q_2} + \frac{L_2 \omega_0}{R_L} \quad \text{[Equation 5]}$$

$$k_{mC} = \frac{1}{Q_2} + \frac{L_2 \omega_0}{R_L} \quad \text{[Equation 6]}$$

As described above, Equation 6, which is derived by transforming Equation 1 showing the critical magnetic coupling coefficient $k_{mC}$, is also the sum of the first term and second term. Thus, the value of Equation 6 can be made small if both the first term and the second term can be made small. As described earlier, regarding the first term, since $1/Q_2$ is preferably made small, it can be understood that $Q_2$, which represents the quality factor of the power reception side coil 21, should be a large value. In addition, regarding the second term, it can be understood that the self-inductance L2 of the power reception side coil 21 is preferably made small and the resonant frequency ω0 is preferably made small, while the resistive load $R_L$ of the wireless power supply system is preferably made large.

The above described fact determines the approach. For example, if the critical magnetic coupling coefficient $k_{mC}$ should be 0.1 or less, at least $1/Q_2$, which is the first term of Equation 6, must be less than 0.1. Thus, $Q_2$, which represents the quality factor of the power reception side coil 21, must be greater than 10. In practice, $Q_2$ is made 100 or greater to make the first term 0.01 or less. In addition, the self-inductance L2 of the power reception side coil 21 is made 200 μH (microhenries) or less, the resonant frequency ω0 is made 200 kHz or less, the resistive load $R_L$ is made 100 ohms or greater, and at least the second term of Equation 6 is made 0.2 or less.

For example, if the critical magnetic coupling coefficient $k_{mC}$ in Equation 6 is 0.2, it can be understood based on the graphs in FIGS. 7A and 7B that the PT symmetry is maintained and the output electric power can be constantly supplied from the transmission side external device 19 to the reception side internal device 29 when the transmission distance between the two coils is within approximately 5 cm and the position displacement is within approximately 4 cm (approximately ±4 cm) in the left-right direction.

For example, if the critical magnetic coupling coefficient $k_{mC}$ in Equation 6 is 0.3, it can be understood based on the graphs in FIGS. 7A and 7B that the PT symmetry is maintained and the output electric power can be constantly supplied from the transmission side external device 19 to the reception side internal device 29 when the transmission distance between the two coils is within approximately 3 cm and the position displacement is within approximately 2 cm (approximately ±2 cm) in the left-right direction.

As described earlier, the parameters (resonant frequency ω0, quality factor $Q_2$ of the power reception side coil 21, self-inductance L2 of the power reception side coil 21, resistive load $R_L$ of the wireless power supply system) are set so that the first term in Equation 6 is 0.01 or less, the second term is 0.2 or less and the critical magnetic coupling coefficient $k_{mC}$ calculated by Equation 6 is 0.2 or less. Thus, the PT symmetry is maintained and the output power can be constantly supplied from the transmission side external device 19 to the reception side internal device 29 even when the distance between the two coils changes or the positions are displaced as long as the transmission distance between the two coils is within approximately 5 cm and the position displacement is within approximately 4 cm (approximately ±4 cm) in the left-right direction. Consequently, the electric power can be supplied stably from the external device 19 installed outside the human body to the internal device 29 installed inside the human body.

Accordingly, the wireless power supply system using the PT symmetry according to the first embodiment of the present invention is sufficiently applicable to artificial devices such as an artificial heart installed in the human body.

Furthermore, if the parameters can be specified so that the critical magnetic coupling coefficient $k_{mC}$ in Equation 6 becomes 0.05 or less, the PT symmetry can be maintained and the output electric power can be supplied stably from the transmission side external device 19 to the reception side internal device 29 even when the distance between the two coils changes or the positions are displaced as long as the distance between the two coils is within approximately 10 cm and the position displacement is within approximately 7 cm (approximately ±7 cm) in the left-right direction. Thus, the restrictions of the movement of human and the installation positions of external device 19 and internal device 29 are further relaxed. Consequently, a user-friendly wireless power supply system can be provided.

According to the experiment, in order to maintain the PT symmetry of the first embodiment of the present invention, $Q_2$, which is the Q value of the power reception side coil 21, should be high. Thus, $Q_2$ is preferably larger than at least Q1, which is the Q value of the power transmission side coil 11.

As described earlier, the PT symmetry cannot be maintained over long distances unless the self-inductance L2 of the power reception side coil 21 is small. Thus, L2 needs to be small and L2 is preferably kept at 50 pH or less.

As described above, since the parameters (e.g., quality factor Q value, inductance, resonant frequency, resistive load) are specified so that the critical magnetic coupling coefficient $k_{mC}$ becomes as small as possible, the PT symmetry can be maintained and the output electric power can be supplied continuously to the reception internal device 29 even when the distance between the power transmission side coil 11 and the power reception side coil 21 changes or the positions are displaced.

As described above, in the wireless power supply system using the PT symmetry of the first embodiment of the present invention, the power transmission side resonance circuit 12 is formed by connecting the power transmission side resonance capacitor $C_1$ in series with the power transmission side coil 11, the power reception side resonance circuit 22 is formed by connecting the power reception side resonance capacitor $C_2$ to the power reception side coil 21, and the resonant frequency ω0 of the resonant circuits is matched between the power transmission side and the power reception side. In addition, the parameters (e.g., quality factor Q value, inductance, resonant frequency, resistive load) are specified so that the PT symmetry is maintained in the wireless power supply system of the present invention within the expected transmission distance between the power transmission side coil 11 and the power reception side coil 21 (i.e., the value in Equation 6 becomes as small as possible).

Furthermore, since the strength of interaction between the power transmission side coil 11 and the power reception side coil 21 is important, the shapes of both coils are preferably the same and the sizes of both coils are preferably approximately same. Alternatively, the power transmission side coil 11 is preferably larger than the power reception side coil 21 to maintain the strong mutual influence relationship. In practice, as shown in FIG. 6A, the coils having similar size with each other are used.

Although the explanation is repeated, the coil shape is preferably solenoid-type as described earlier. There are two coil shapes: a solenoid type; and a spiral type. The PT symmetry can be preserved with either type. Although a spiral-type coil is generally used, high frequency cannot be used since the wireless power supply system of the present invention is the transcutaneous power transmission system for supplying the electric power to the artificial device installed inside the human body in a noncontact manner. Therefore, low frequencies should be used. The solenoid-type coil tends to have higher Q value than the spiral-type coil at low frequencies. When the Q value is high, the PT symmetry can be preserved over longer distances. Thus, the solenoid-type coil is preferable.

In order to supply the electric power continuously without interruption even when the distance and the angle between the power transmission side coil 11 and the power reception side coil 21 changes in the wireless power supply system using the PT symmetry of the first embodiment of the present invention, the distance between the power reception side coil 21 provided in the internal device group 20 including a ventricular assist device (artificial heart control circuit 26 and artificial heart 27) and the power transmission side coil 11 provided in the external device group 10 is preferably 10 cm or less.

As described earlier, the maximum transmission distance over which the PT symmetry can be preserved tends to increase as the coil size becomes larger. The area where the coils face each other as shown in FIG. 4 and FIG. 6A is called the coil surface. Although the maximum transmission distance between the coils depends on the parameter settings, when the area of the coil surface is (5 cm×3 cm=15 cm2), for example, the maximum transmission distance between the coils is predicted to be approximately 5 cm if the parameters are specified so that the critical magnetic coupling coefficient $k_{mC}$ in Equation 6 is 0.2 or less. Therefore, in this case, the distance between the power transmission side coil 11 and the power reception side coil 21 is preferably within 5 cm. Namely, the external device 19 should be installed in the position within 5 cm from the power reception side coil 21 (internal device 29) so that the distance between the power reception side coil 21 installed inside the human body and the power transmission side coil 11 installed in the external device 19 is within 5 cm.

When the distance between the external device group 10 and the power reception side coil 21 is within 5 cm (i.e., the distance between the power transmission side coil 11 and the power reception side coil 21 is within 5 cm), the electric power is supplied continuously from the power transmission side coil 11 to the power reception side coil 21 even when the distance changes. Thus, the electric power can be wirelessly supplied to the ventricular assist device continuously without interruption of the supply of the electric power from the external device group 10 to the ventricular assist device (artificial heart control circuit 26 and artificial heart 27) in the internal device group 20.

Therefore, specifically, in the case of the ventricular assist device (artificial heart control circuit 26 and artificial heart 27) for assisting the blood circulation by attaching a motor-driven pump under the actual heart and installing the power reception side coil 21 in the internal device group 20 in which the ventricular assist device is installed, the power reception side coil 21 is positioned around just below the navel of the human body. When the waist belt 53 such as an ordinarily trouser belt is wound around the waist of the human body and the external device group 10 is attached around a buckle portion of the waist belt 53, the power transmission side coil 11 installed inside the external device group 10 is positioned within 5 cm distance from the power reception side coil 21 located inside the human body. Thus, the electric power is continuously supplied from the power transmission side coil 11 to the power reception side coil 21. Consequently, the electric power can be continuously supplied from the external device group 10 to the ventricular assist device (artificial heart control circuit 26 and artificial heart 27) located inside the internal device group 20 without interruption of the supply of the electric power. Thus, the electric power can be wirelessly supplied to the ventricular assist device continuously.

When the above described structure which utilizes the physical phenomenon of the PT symmetry for the control of the electric power, the configuration of the external device such as the power transmission side device located outside the human body and the internal device become simplified and the patient himself/herself can easily replace the battery for supplying the electric power to the external device. The above described operation of replacing the battery is required periodically. In the conventional wireless power supply system, the power supply is temporarily interrupted due to the position displacement during the operation of replacing the battery. Thus, it is very difficult for the patient to perform the replacement of the battery by himself/herself. Even when the others assist the replacement, the operation should be performed carefully and the operation cannot be performed smoothly unless the operator is experienced.

In the wireless power supply system of the first embodiment of the present invention, the electric power is continuously supplied to the power reception side coil 21 without any problems even when the positions are displaced to a certain degree. For example, as shown by the broken lines in FIG. 3, the operation of replacing the battery can be finished in a unit of the external device group 10 simply by winding a waist belt 53' provided with a new external device group 10 containing a new battery (external power source 5) under the original waist belt 53 where the existing external device group 10 is fixed and then removing the original waist belt 53. Thus, the patient can easily replace the battery by himself/herself.

Furthermore, when the above described battery replacement method is used, the waist belt 53 (or 53') can be fixed in the position slightly shifted up or down from the previous position. Thus, even in seasons like summer when heat rash tends to develop under the belt, such concerns can be eliminated. In addition, the battery can be replaced cleanly by simply setting a new belt in a different position up or down when the battery runs out and then removing the previous belt. Thus, patient can easily replace the battery by themselves. Furthermore, the patient can take baths with only the components below the belt or slightly shift the belt to wipe their body. Thus, significant benefits can be obtained in sanitation.

Furthermore, when the waist belt 53 (or 53') is worn too loosely, the waist belt 53 (or 53') may rotate to increase the distance between the external device group 10 provided with the power transmission side coil 11 and the ventricular assist device (artificial heart control circuit 26 and artificial heart 27) located inside the internal device group 20. Considering the above described situation, it is possible to provide a plurality of power transmission side coils 11 inside the external device group 10 to cope with the position displacement in the rotation direction of the belt. In this case, there are a plurality of power transmission side coils 11 and one power reception side coil 21. It is possible to provide a function of automatically selecting the power transmission side coil 11 paired with the power reception side coil 21 (function of selecting the power transmission side coil 11 located at the shortest distance from the power reception side coil 21 to provide the electric power from the selected power transmission side coil 11).

In the above described case where there are a plurality of power transmission side coils 11 and one power reception side coil 21, it is common to switch off the resonant circuits of the unused power transmission side coils 11. However, it is also possible to transmit power from a plurality of power transmission side coils 11 to one power reception side coil 21. On the contrary, if there are one power transmission side coil 11 and a plurality of power reception side coils 21, the frequency cannot be automatically adjusted. Thus, it is difficult to maintain the PT symmetry and such a configuration cannot be adopted.

In the first embodiment, the explanation is made by using the example of the ventricular assist device as the device of wirelessly supplying the electric power to the internal device for driving the artificial device installed inside the human body. However, the wireless power supply system of the present invention can be applied to other artificial devices such as an artificial kidney, an artificial pancreas, an artificial inner ear and an artificial eye without being limited to the artificial heart (ventricular assist device).

Specifically, the artificial kidney filters the blood and requires a power source (electric power) to drive the pump for sending the blood. The artificial pancreas detects the glucose concentration in the blood and discharges a necessary amount of insulin into the blood. The artificial pancreas requires a sensor and a power source (electric power) to drive the pump for discharging the insulin. The artificial inner ear converts sound to electricity through a microphone, amplifies the electricity, processes the information and transmits it to nerves through electrical stimulation. The artificial inner ear requires a power source (electric power) to drive the circuit of the artificial inner ear. The artificial eye converts image information to electricity through a semiconductor imaging device, processes the information and transmits it to nerves through electrical stimulation. The artificial eye requires a power source (electric power) to drive the circuit of the artificial eye.

As described above, in the cases of the artificial devices other than the artificial heart and the ventricular assist device, similar to the artificial heart, the power source (electric power) is required for the driving unit for driving the pump or using the current for sending the signal to nerves. Thus, the method of wirelessly transmitting the electric power from the outside of the human body without forming the hole on the human body and without connecting wires from the outside of the human body is preferred. Therefore, when the wireless power supply system using the PT symmetry of the first embodiment of the present invention is applied to the above described artificial devices, there is no need to worry about the position displacement and the angle displacement. Thus, the usability of the artificial device can be improved.

As described above, the wireless power supply system of the first embodiment of the present invention utilizes the PT symmetry. Thus, the electric power can be wirelessly transmitted to the internal device for driving the artificial device installed inside the human body without forming holes on the human body and without connecting wires from outside of the human body. Therefore, a risk of infection of the patient can be eliminated. In addition, the adjustment of the position and the angle between the power transmission side coil and the power reception side coil is not required for transmitting the electricity to the internal device installed inside the human body. Thus, the electric power can be continuously supplied and high transmission efficiency can be maintained even when the positions of the power transmission side coil and the power reception side coil are displaced to a certain degree. Therefore, the electric power can be wirelessly supplied continuously. Furthermore, the physical phenomenon of the PT symmetry is utilized for the control of the electric power. Thus, the configuration of the external device and the internal device can be simplified.

Note that the modification of the configuration and the omission of configuration can be arbitrarily performed in the embodiments within the scope of the invention.

INDUSTRIAL APPLICABILITY

The wireless power supply system of the present invention can be applied to various artificial devices installed inside the human body such as an artificial kidney, an artificial pancreas, an artificial inner ear and an artificial eye in addition to the artificial heart (ventricular assist device), for example.

DESCRIPTION OF SYMBOLS

- 1: conventional ventricular assist device
- 2: cable such as electric wire
- 3: hole bored in human body (abdomen)
- 4: controller located outside of human body
- 5: external power source (power source located outside of human body)
- 10: external device group
- 11: power transmission side coil
- 12: power transmission side resonance circuit
- 13: inverter circuit
- 19: external device
- 20: internal device group

21: power reception side coil
22: power reception side resonance circuit
23: rectifier circuit
24: DC/DC converter
25: storage battery
26: artificial heart control circuit (artificial device control circuit)
27: artificial heart (artificial device)
29: internal device
51: shoulder belt
52: crossbody belt
53, 53': waist belt
100, 200: magnetic core
101, 102, 201, 202: magnetic pole

The invention claimed is:

1. A wireless power supply system, comprising:

an internal device installed inside a human body for driving an artificial device installed inside the human body; and an external device installed outside the human body, wherein an electric power is configured to be supplied from the external device to the internal device in a noncontact manner using Parity-Time symmetry, an external power source is connected to the external device, an inverter circuit is provided in the external device for converting a DC voltage supplied from the external power source into an AC voltage, a power transmission side resonance circuit and a power transmission side coil are provided in the external device for converting the AC voltage converted by the inverter circuit into an AC magnetic field and transmitting the electric power to the internal device, a power reception side coil and a power reception side resonance circuit are provided in the internal device for interlinking the AC magnetic field generated in the power transmission side coil, a rectifier circuit is provided in the internal device for converting the AC voltage outputted from the power reception side coil and the power reception side resonance circuit into the DC voltage, the artificial device is configured to be driven by DC power converted by the rectifier circuit, the power transmission side resonance circuit is formed by connecting the power transmission side coil and a power transmission side resonance capacitor in series with each other and connecting the power transmission side coil and the power transmission side resonance capacitor with the inverter circuit, the power reception side resonance circuit is formed by connecting the power reception side coil with at least one of power reception side resonance capacitors, and resonance frequencies are matched with each other between the power transmission side resonance circuit and the power reception side resonance circuit.

2. The wireless power supply system according to claim 1, wherein when the resonance frequency is ω0, a quality factor of the power reception side coil is Q2, a self-inductance of the power reception side coil is L2 and a resistive load of the wireless power supply system is RL, the resonance frequency ω0, the quality factor Q2 of the power reception side coil, the self-inductance L2 of the power reception side coil and the resistive load RL of the wireless power supply system are specified so that a critical magnetic coupling coefficient kmC which is a critical value of a magnetic coupling coefficient between the power transmission side coil and the power reception side coil shown in Equation 1 is 0.2 or less.

$$k_{mC} = \frac{1}{Q_2} + \frac{L_2\omega_0}{R_L} \quad \text{[Equation 1]}$$

3. The wireless power supply system according to claim 1, wherein the power transmission side coil and the power reception side coil are a solenoid type coil formed by winding a coil around a magnetic core made of a soft magnetic material, the magnetic core includes a magnetic pole having an approximately rectangular parallelepiped shape at both ends of the magnetic core, the coil is not wound around the magnetic pole, and the magnetic pole is formed so that an area of a facing surface of the magnetic pole when the power transmission side coil and the power reception side coil face each other is larger than the area of the other surfaces of the magnetic pole.

4. The wireless power supply system according to claim 1, wherein the internal device is further provided with a storage battery for temporarily storing the DC power converted by the rectifier circuit, and the artificial device is configured to be driven by the electric power stored in the storage battery.

* * * * *